United States Patent
Dehkhoda et al.

(10) Patent No.: US 11,015,986 B2
(45) Date of Patent: May 25, 2021

(54) TEMPERATURE SENSOR

(71) Applicant: University of Newcastle Upon Tyne, Tyne and Wear (GB)

(72) Inventors: Fahimeh Dehkhoda, Tyne and Wear (GB); Patrick Degenaar, Tyne and Wear (GB); Ahmed Soltan, Tyne and Wear (GB)

(73) Assignee: University of Newcastle Upon Tyne, Tyne and Wear (GB)

( * ) Notice: Subject to any disclaimer, the term of this patent is extended or adjusted under 35 U.S.C. 154(b) by 192 days.

(21) Appl. No.: 16/065,660

(22) PCT Filed: Dec. 22, 2016

(86) PCT No.: PCT/EP2016/082433
§ 371 (c)(1),
(2) Date: Jun. 22, 2018

(87) PCT Pub. No.: WO2017/109103
PCT Pub. Date: Jun. 29, 2017

(65) Prior Publication Data
US 2019/0003898 A1    Jan. 3, 2019

(30) Foreign Application Priority Data
Dec. 23, 2015   (GB) .................. 1522790

(51) Int. Cl.
*G01K 7/01* (2006.01)
*G01K 7/42* (2006.01)
(Continued)

(52) U.S. Cl.
CPC .............. *G01K 7/01* (2013.01); *A61B 5/01* (2013.01); *A61B 5/4041* (2013.01);
(Continued)

(58) Field of Classification Search
CPC ...... G01K 7/01; G01K 7/427; G01K 2211/00; G01K 2217/00; A61B 5/4848;
(Continued)

(56) References Cited

U.S. PATENT DOCUMENTS 5,445,608 A * 8/1995 Chen .................... A61N 5/0601
                                                        604/19
2007/0075370 A1* 4/2007 Boerstler ................. G01K 7/01
                                                        257/355
(Continued)

OTHER PUBLICATIONS

Barrett, J. M. et al., "Blockage of pathological retinal ganglion cell hyperactivity improves optogenetically evoked light responses in rd1 mice," Fronteirs in Cellular Neuroscience, vol. 9, Article 330, Aug. 25, 2015, 14 pages.
(Continued)

*Primary Examiner* — Amanda K Hulbert
*Assistant Examiner* — Natasha Patel
(74) *Attorney, Agent, or Firm* — Kilpatrick Townsend & Stockton

(57) ABSTRACT

A temperature sensor comprising a light emitter, an electrical circuit for applying a reverse bias voltage across the light emitter and for measuring a reverse current, and means for calculating a temperature from the measured reverse current.

26 Claims, 17 Drawing Sheets

Sensor block diagram

(51) Int. Cl.
  *A61N 5/06* (2006.01)
  *A61B 5/01* (2006.01)
  *A61B 5/00* (2006.01)
  *A61N 5/067* (2006.01)
(52) U.S. Cl.
  CPC .......... *A61B 5/4848* (2013.01); *A61N 5/0601* (2013.01); *A61N 5/0622* (2013.01); *G01K 7/427* (2013.01); *A61B 2562/0271* (2013.01); *A61N 2005/067* (2013.01); *A61N 2005/0612* (2013.01); *A61N 2005/0627* (2013.01); *A61N 2005/0652* (2013.01); *G01K 2211/00* (2013.01); *G01K 2217/00* (2013.01)
(58) Field of Classification Search
  CPC . A61B 5/4041; A61B 5/01; A61B 2562/0271; A61N 5/0601; A61N 5/0622; A61N 2005/0612; A61N 2005/0627; A61N 2005/0652; A61N 2005/067
  See application file for complete search history.

(56) References Cited

U.S. PATENT DOCUMENTS

| | | | |
|---|---|---|---|
| 2010/0004892 | A1 | 1/2010 | Lin et al. |
| 2010/0190229 | A1* | 7/2010 | Zhang ................ A61K 48/0058 435/173.1 |
| 2011/0125077 | A1* | 5/2011 | Denison ............... A61N 5/0601 604/20 |
| 2015/0117494 | A1 | 4/2015 | Caldara |
| 2015/0148643 | A1 | 5/2015 | Small et al. |
| 2015/0202456 | A1* | 7/2015 | Andersen ........... A61K 41/0057 604/20 |

OTHER PUBLICATIONS

Barrett, J. et al., "Optogenetic approaches to retinal prosthesis," Visual Neuroscience, vol. 31, No. 4-5, pp. 345-354, 2014.
Berlinguer-Palmini, R. et al., "Arrays of MicroLEDs and Astrocytes: Biological Amplifiers to Optogenetically Modulate Neuronal Networks Reducing Light Requirement," PLoS One, vol. 9, No. 9, 2014.
Broichhagen, J. et al., "Optical Control of Insulin Secretion Using an Incretin Switch," Angewandte Chemie International Edition, vol. 54, 2015.
Cao, X. A. et al., "Diffusion and Tunneling Currents in GaN/InGaN Multiple Quantum Well Light-Emitting Diodes," IEEE Electron Device Letters, vol. 23, No. 9, 2002.
Cho, A. Y., "Advances in molecular beam epitaxy (MBE)," Journal of Crystal Growth, vol. 111, No. 1, pp. 1-13, 1991.
Crepaldi, P. C. et al., "Low-voltage, low-power, high linearity front-end thermal sensing element," Electronics Letters, vol. 46, No. 18, pp. 1271-1272, 2010.
Dehkhoda, F. et al., "Self-sensing of temperature rises on light emitting diode based optrodes," Journal of Neural Engineering, No. 15, Published Jan. 25, 2018, 12 pages.
Du, J. et al., "Multiplexed, High Density Electrophysiology with Nanofabricated Neural Probes," PLoS ONE, vol. 6, Issue 10, Oct. 2011, 13 pages.
Fujii, T. et al., "Effects of heating on electrical activities of guinea pig olfactory cortical slices," European Jurnal of Physiology, vol. 392, No. 3, p. 257-260, 1982.
Furuya, K. et al, "GaInAsP/InP organometallic vapor phase epitaxy for research and fabrication of devices," International Journal of High Speed Electronics, vol. 1, No. 347-367, 1990, 21 pages.
Heim, R. et al., "Improved green fluorescence," Nature, vol. 373, No. 6516, pp. 663-664, Feb. 23, 1995.
Huang, Y. J. et al., "A Self-Powered CMOS Reconfigurable Multi-Sensor," IEEE Journal of Solid-State Circuits, vol. 49, No. 4, pp. 851-866, 2014.

Koizumi, A. et al., "The manipulation of neural and cellular activities by ectopic expression of melanopsin," Neuroscience Research, vol. 75, No. 1, pp. 3-5, 2013.
Lee, H. Y. et al., "CMOS thermal sensing system with simplified circuits and high accuracy for biomedical application Circuits and Systems," in Proceedings of IEEE International Symposium on Circuits and Systems, ISCAS, pp. 4367-4370, 2006.
Liu, W. J., "Room temperature continuous wave lasing of electrically injected GaN-based vertical cavity surface emitting lasers." Applied Physics Letters, vol. 104, No. 251116, 2014, 5 pages.
Matsumi, N. et al., "Thermal Damage Threshold of Brain Tissue—Histological Study of Heated Normal Monkey Brains—" *Neurol Med Chir* (Tokyo) vol. 34, pp. 209-215, 1994.
Nagel, G. et al., "Channelrhodopsin-2, a directly light-gated cation-selective membrane channel," National Academy of Science, vol. 100, pp. 13940-13945, 2003.
Oheim, M. et al., "New red-fluorescent calcium indicators for optogenetics, photoactivation and multi-color imaging," Biochimica et Biophysica Acta, vol. 1843, No. 10, pp. 2284-2306, 2014.
Okazaki, Y. et al., "Heat From an Implanted Power Source is Mainly Dissipated by Blood Perfusion," *Asaio J.*, vol. 43, pp. M585-M588.
Opie, N. L., et al., "Retinal Prosthesis Safety: Alterations in Microglia Morphology due to Thermal Damage and Retinal Implant Contact," Investigative Ophthalmology & Visual Science, Nov. 2012, vol. 53, No. 12, pp. 7802-7812.
Salem, S. B. et al., "A High Performances CMOS CCII and High Frequency Applications," Analog Integrated Circuits and Signal Processing, vol. 49, pp. 71-78, 2006.
Shoham, S. et al., "Rapid neurotransmitter uncaging in spatially defined patterns," Nature methods, vol. 2, pp. 837-843, 2005.
Soboleski, M. R. et al., "Green fluorescent protein is a quantitative reporter of gene expression in individual eukaryotic cells," *FASEB J.* Author manuscript; available in PMC Oct. 5, 2005, 18 pages.
Stujenske, J. M., "Modeling the Spatiotemporal Dynamics of Light and Heat Propagation for In Vivo Optogenetics," Cell Reports, vol. 12, Jul. 21, 2015, pp. 525-534.
Wu, B. et al., "Junction-Temperature Determination in InGaN Light-Emitting Diodes Using Reverse Current Method," IEEE Transaction on Electronc Devices, vol. 60, No. 1, 2013.
Wu, F. et al., "Monolithically Integrated µLEDs on Silicon Neural Probes for High-Resolution Optogenetic Studies in Behaving Animals," Neuron vol. 88, Dec. 16, 2015, pp. 1136-1148.
Xi, Y. et al., "Junction-temperature measurement in GaN ultraviolet light-emitting diodes using diode forward voltage method," Applied Physics Letters, vol. 85, No. 12, pp. 2163-2165, 2004.
Yizhar, O. et al., "Optogenetics in Neural Systems," Neuron Primer vol. 71, Jul. 14, 2011, pp. 9-34.
Zhang, F. et al., "Multimodal fast optical interrogation of neural circuitry," Nature, vol. 446, No. 7136, p. 633-639, 2007.
Alzaher et al., "A CMOS Fully Balanced Second-Generation Current Conveyor", IEEE Transactions on Circuits and Systems II, Analog and Digital Signal Processing, vol. 50, No. 6, Oct. 28, 2000, 278-287.
Bianchi et al., "CMOS-compatible smart temperature sensors", Microelectronics Journal 29, 1998, 627-636.
Cao et al., "An Intergrated µLED Optrode for Optogenetic Stimulation and Electrical Recording", IEEE Transactions on Biomedical Engineering, vol. 60, No. 1, 2012, 225-229.
Chen et al., "Ultrasensitive Fluorescent Proteins for Imaging Neuronal Activity", Macmillan Publishers, Nature, vol. 499, 2013, 295-302.
Dehkhoda, "Smart Optrode for Neural Stimulation and Sensing", Dehkhoda, F & Soltan, Ahmed & Ramezani, Reza & Zhao, H & Liu, Yan & Constandinou, T & Degenaar, Patrick. (2015). Smart optrode for neural stimulation and sensing. 1-4. 10.1109/ICSENS. 2015.7370687., 2015, pp. 1-4.
Demchenko, "Introduction to Fluorescence Sensing", Second Edition, Laboratory of Nanobiotechnology, Palladin Institute of Biochemistry, National Academy of Sciences of Ukraine, 2015, 31 pp.
Deng et al., "A CMOS Smart Temperature Sensor With Single-Point Calibration Method for Clinical Use", IEEE Transactions on Circuits and Systems II, Express Briefs, vol. 63, No. 2, Feb. 2016, 2015, pp. 136-140.

(56) References Cited

OTHER PUBLICATIONS

Goldstein et al., "Summary, Conclusions and Recommendations: Adverse Temperature Levels in the Human Body", L. S. Goldstein, M. W. Dewhirst, M. Repacholi & L. Kheifets (2003) Summary, conclusions and recommendations: adverse temperature levels in the human body, International Journal of Hyperthermia, 19:3, 373-384, DOI: 10.1080/02656730310000907101, 2009, pp. 373-384.

Jung et al., "Leakage Current Analysis of GaN-Based Light-Emitting Diodes Using a Parasitic Diode Model", IEEE Transactions on Electron Devices, vol. 62, No. 10, 2015, pp. 3322-3325.

Kim et al., "Thermal Impact of an Active 3-D Microelectrode Array Implanted in the Brain", IEEE Transactions on Neural Systems and Rehabilitation Engineering, vol. 15, No. 4, 2007, pp. 493-501.

Koizumi et al., "The Manipulation of Neural and Cellular Activities by Ectopic Expression of Melanopsin", Neuroscience Research, vol. 75, Issue 1, Jan. 2013, pp. 3-5.

Lamanna et al., "Stimulus-Activated Changes in Brain Tissue Temperature in the Anesthetized Rat", Metabollic Brain Disease, vol. 4, No. 4, 1989, pp. 1-13.

Maaskant et al., "High-Speed Substrate-Emitting Micro-Light-Emitting Diodes for Applications Requiring High Radiance", Appl. Phys. Express 6, 2013, pp. 022102-1-022102-3.

Mcalinden et al., "Thermal and Optical Characterization of Micro-LED probes for in vivo optogenetic neural stimulation", Optical Society of America, Optics Letters, vol. 38, No. 6, 2013, pp. 992-994.

Pastrana, "Optogenetics: controlling cell function with light", Nature Methods, vol. 8, No. 1, Jan. 2011, pp. 24-25.

Schwaerzle et al., "Miniaturized 3x3 Optical Fiber Array for Optogenetics with Intergrated 460 NM Light Sources and Flexible Electrical Interconnection", Department of Microsystems Engineering (IMTEK), University of Freiburg, Germany, MEMS 2015, Estoril, Portugal, Jan. 18-22, 2015, pp. 18-22.

Seese, "Characterization of Tissue Morphology, Angiogenesis, and Temperature in the Adaptive Response of Muscle Tissue to Chronic Heating", Laboratory Investigation, The United States and Canadian Academy of Pathology, vol. 78, No. 12, p. 1553, 1998, pp. 1553-1563.

Shan et al., "Transporting-Mechanism Analysis of the Reverse Leakage Current in GaInN Light-emitting Diodes", American Institute of Physics, Applied Physics Letters, 99, 2011, pp. 253506-1-253506-3.

Soltan et al., "High Density, High Radiance μLED Matrix for Optogenetic Retinal Prostheses and Planar Neural Stimulation", IEEE Transactions on Biomedical Circuits and Systems, vol. 11, No. 2, 2017, pp. 347-359.

Sparta et al., "Construction of Implantable Optical Fibers for Long-Term Optogeneteic Manipulation of Neural Circuits", Nature America, Inc., Nature Protocols, vol. 7, No. 1, 2012, pp. 12-23.

Udrea et al., "CMOS Temperature Sensors—Concepts, State-of-the-art and Prospects", IEEE, 2008, pp. 31-40.

Wu et al., "An implantable neural probe with monolithically integrated dielectric waveguide and recording electrodes for optogenetics applications", J Neural Eng., vol. 10, No. 5, 056012, 2013, pp. 1-18.

Dong et al., "Opto-electro-thermal optimization of photonic probes for optogenetic neural stimulation", J. Biophotonics 11, 2018, pp. 1-17.

\* cited by examiner

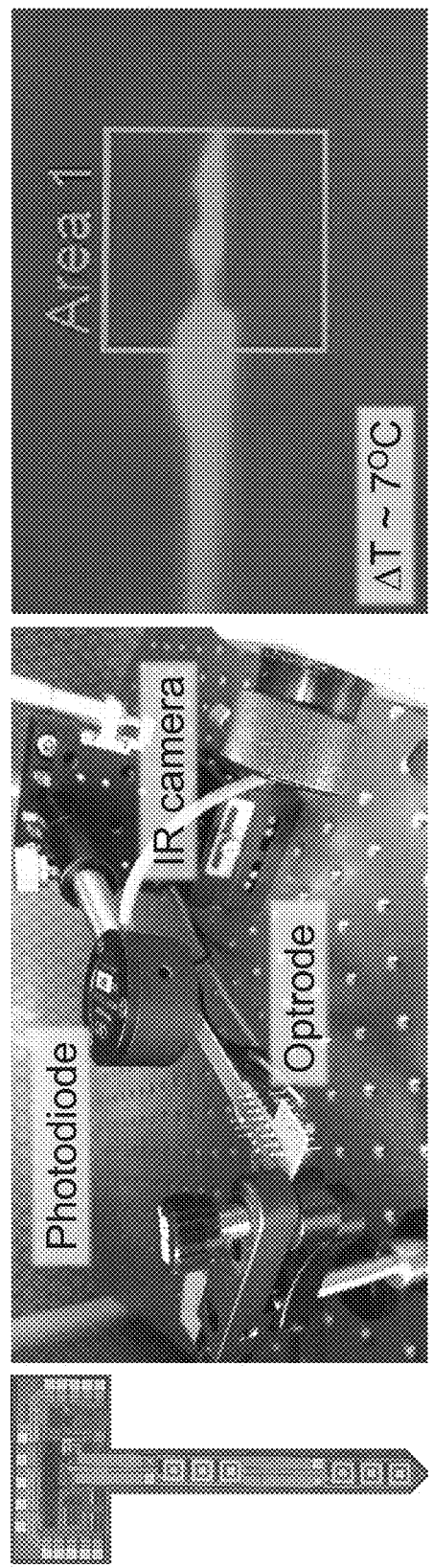
Figure 1 – thermal emission

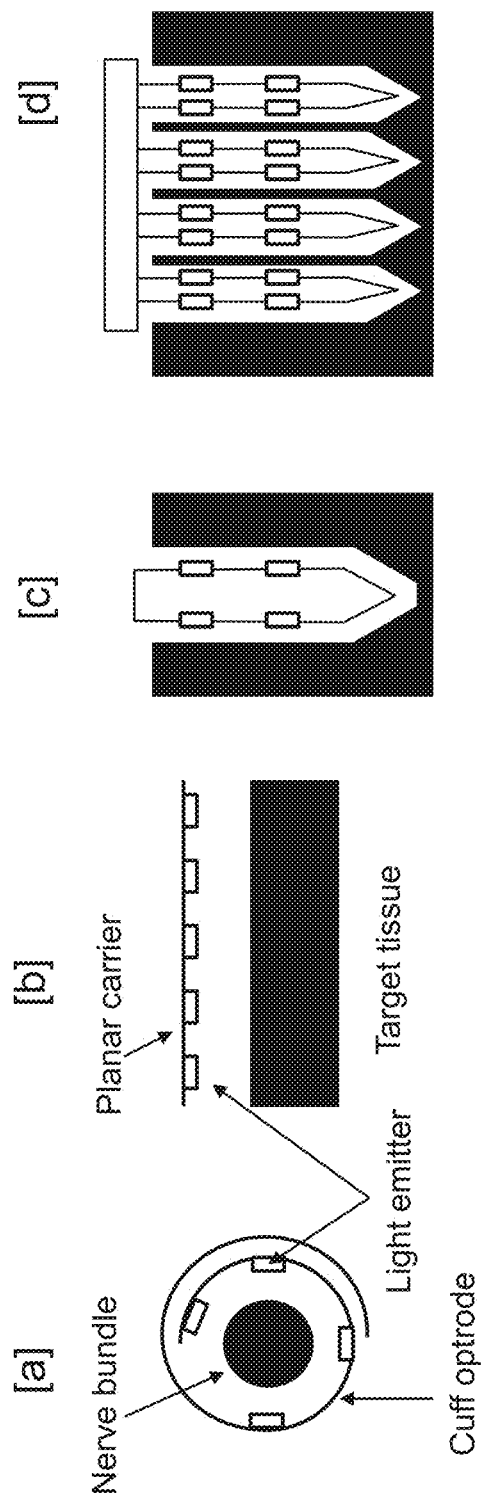
Figure 2 – optrode variants

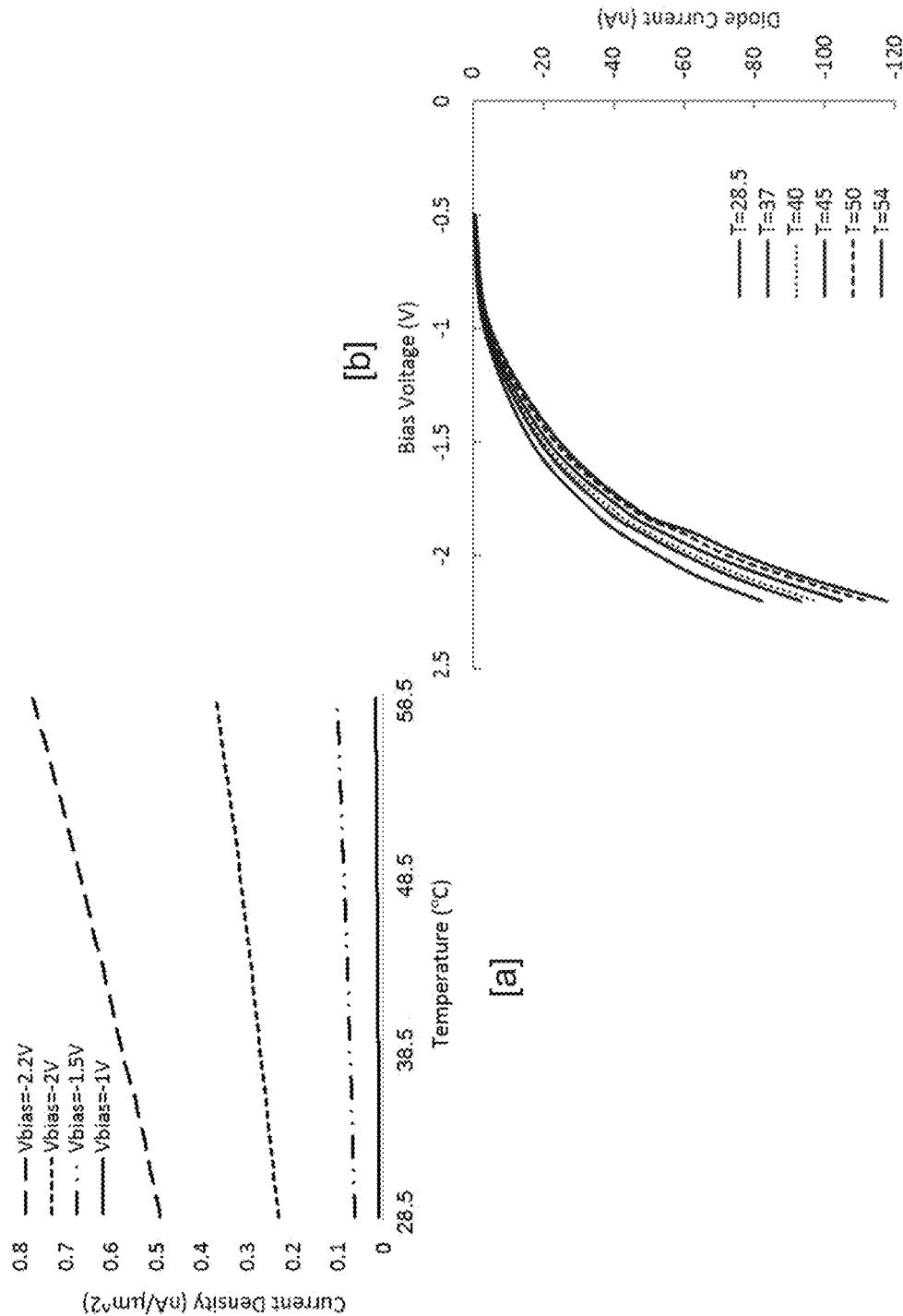

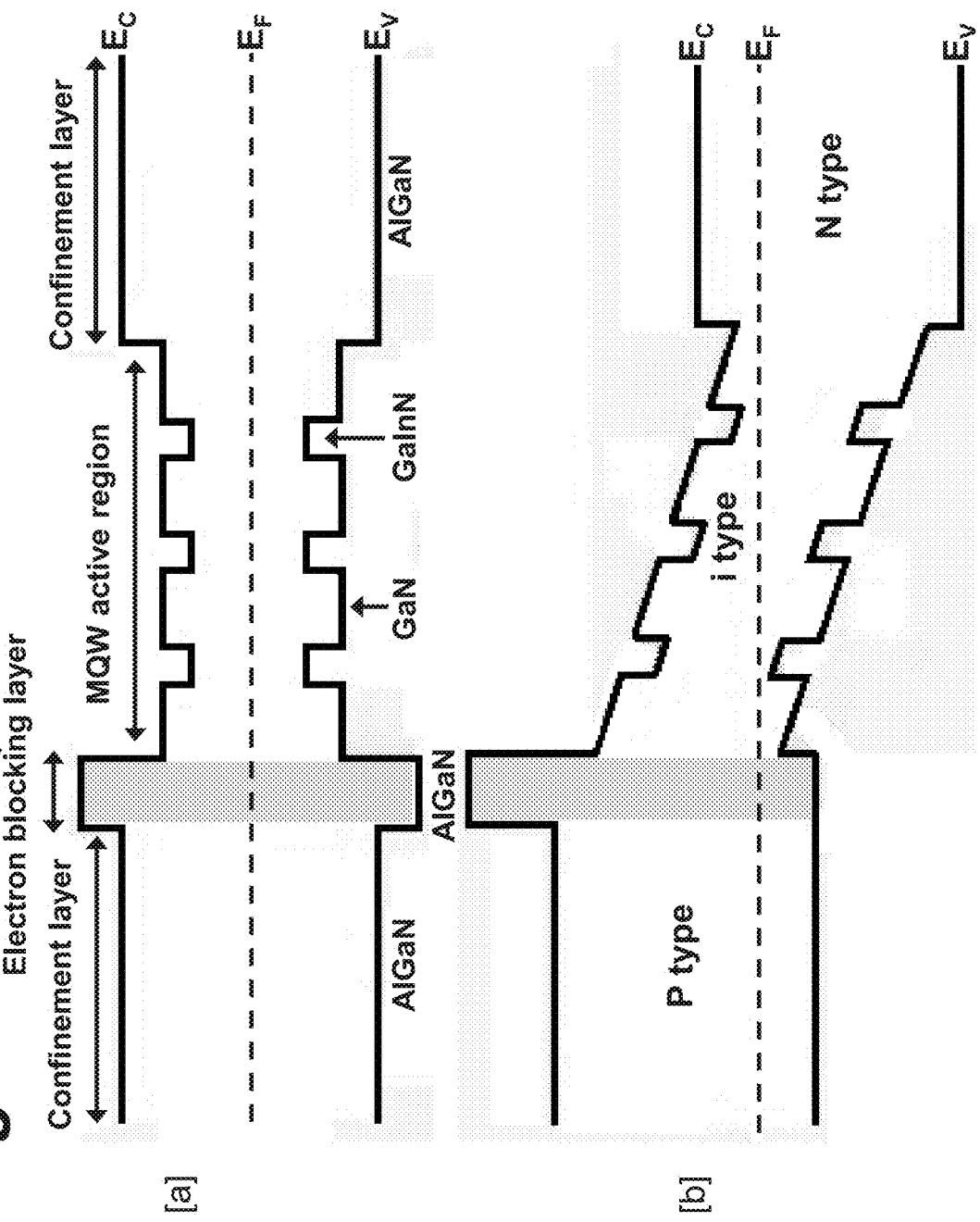

Figure 5 – optrode
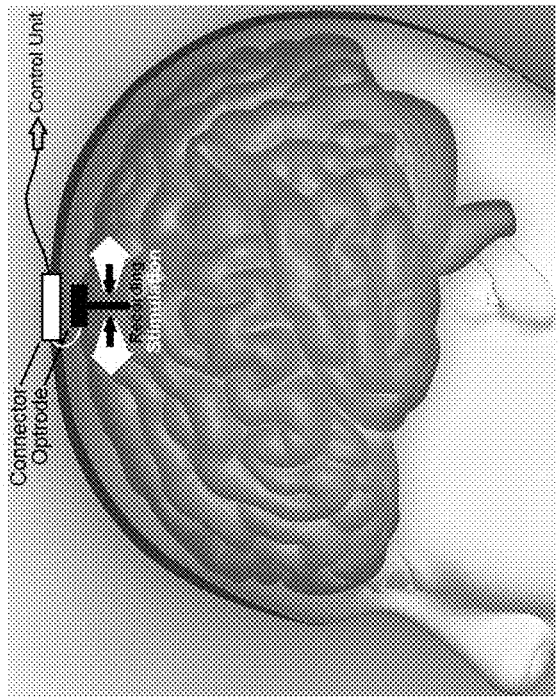
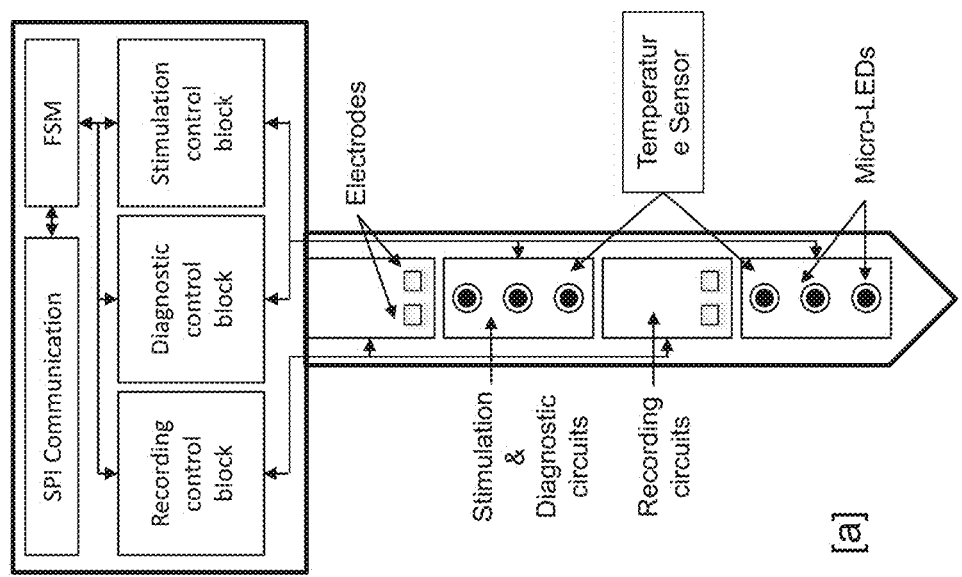

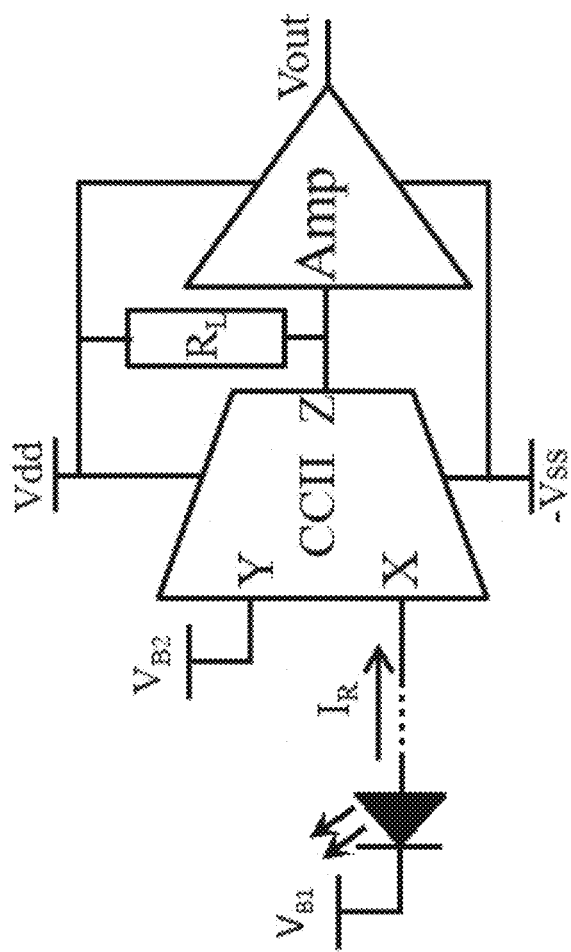
Figure 6 – Sensor block diagram

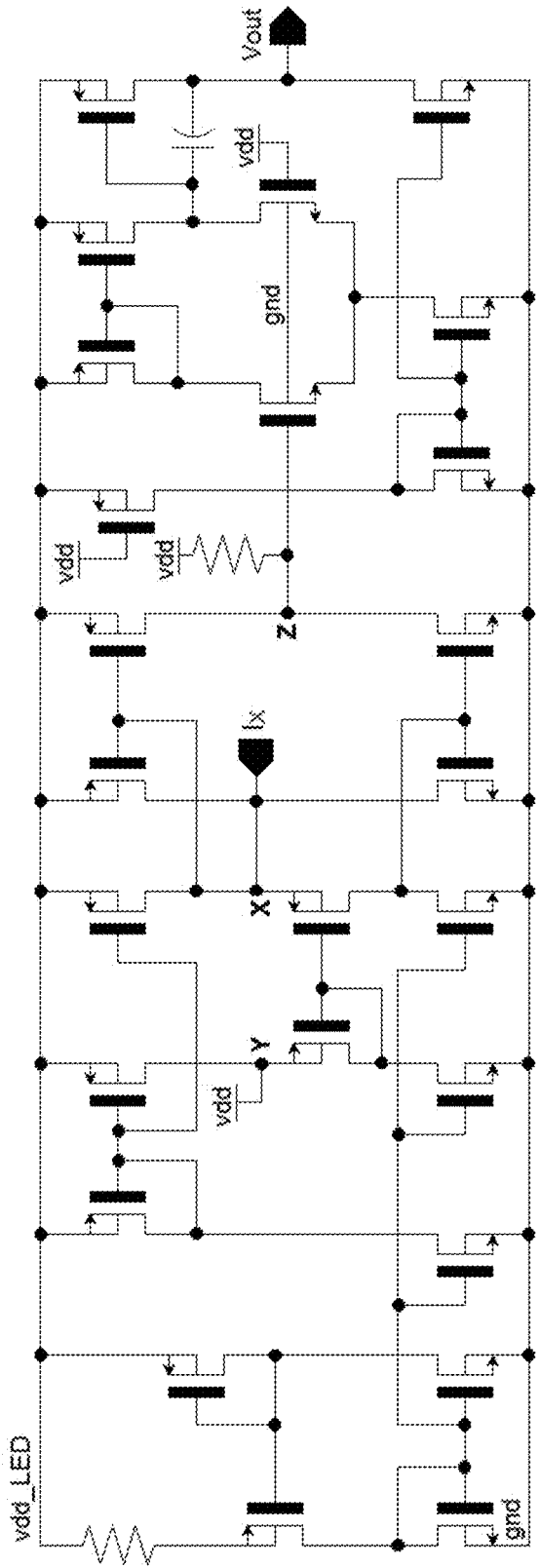
*Figure 7 – Sensor in transistor level*

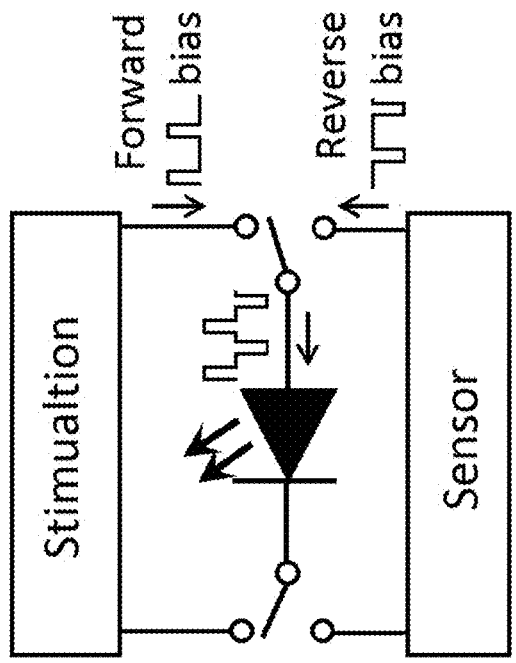
Figure 8a – LED pulses

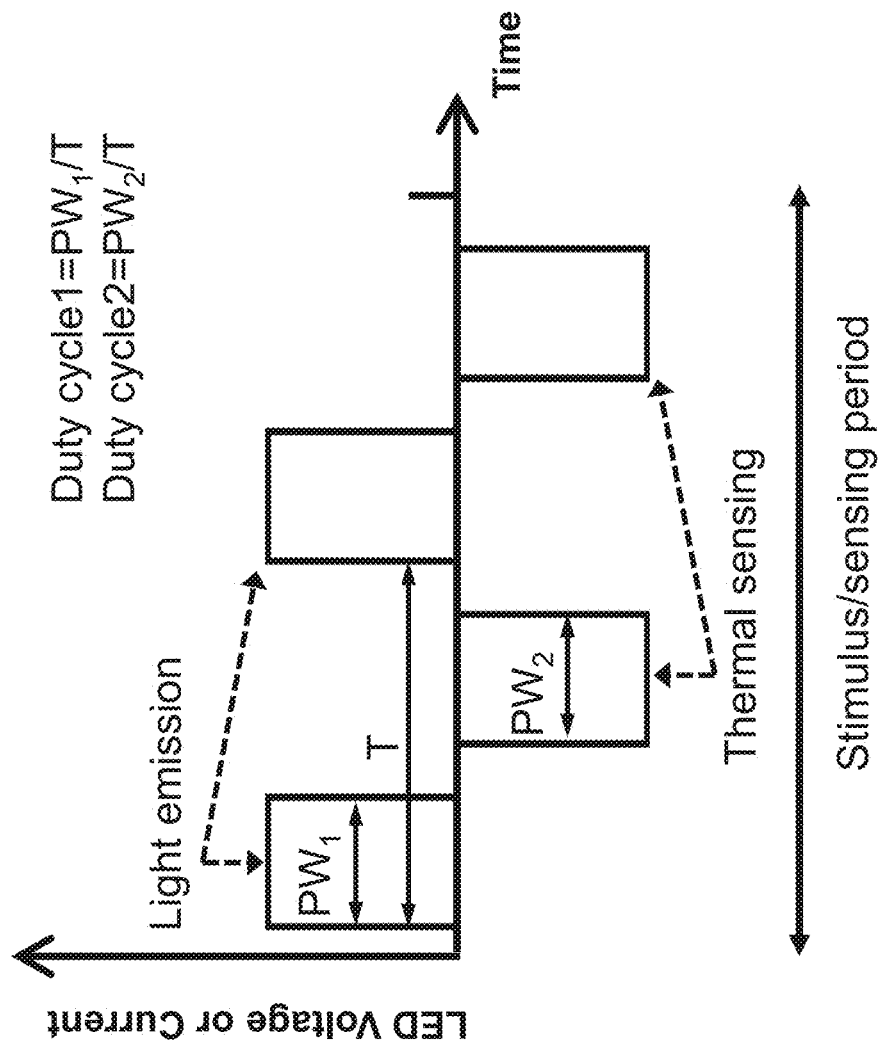

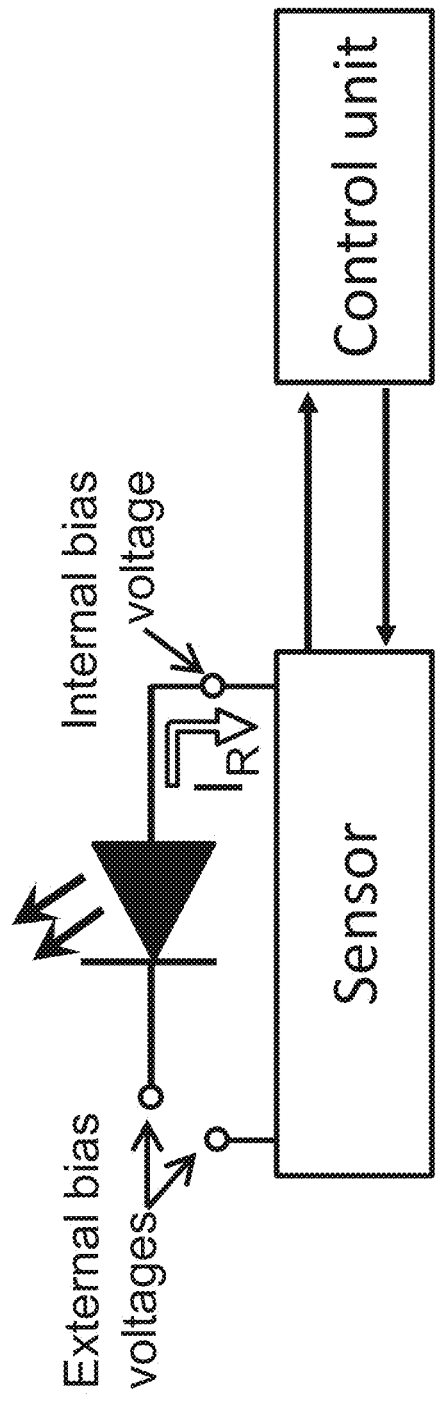
Figure 9a – Sensor control

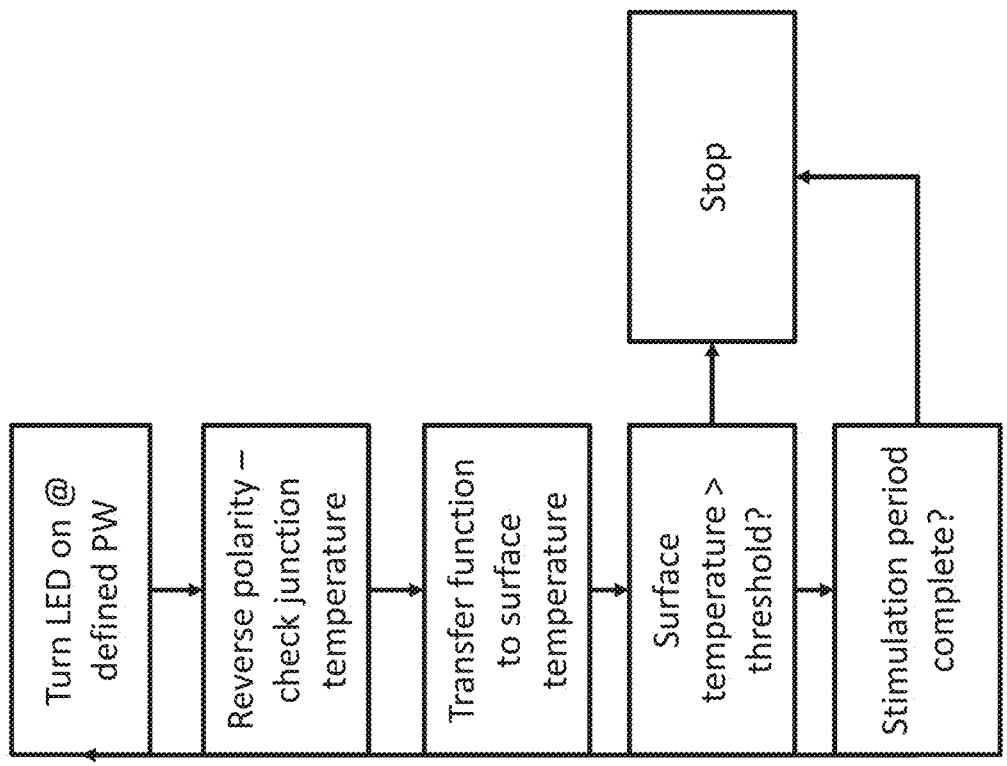
Figure 9b – Sensor control algorithm

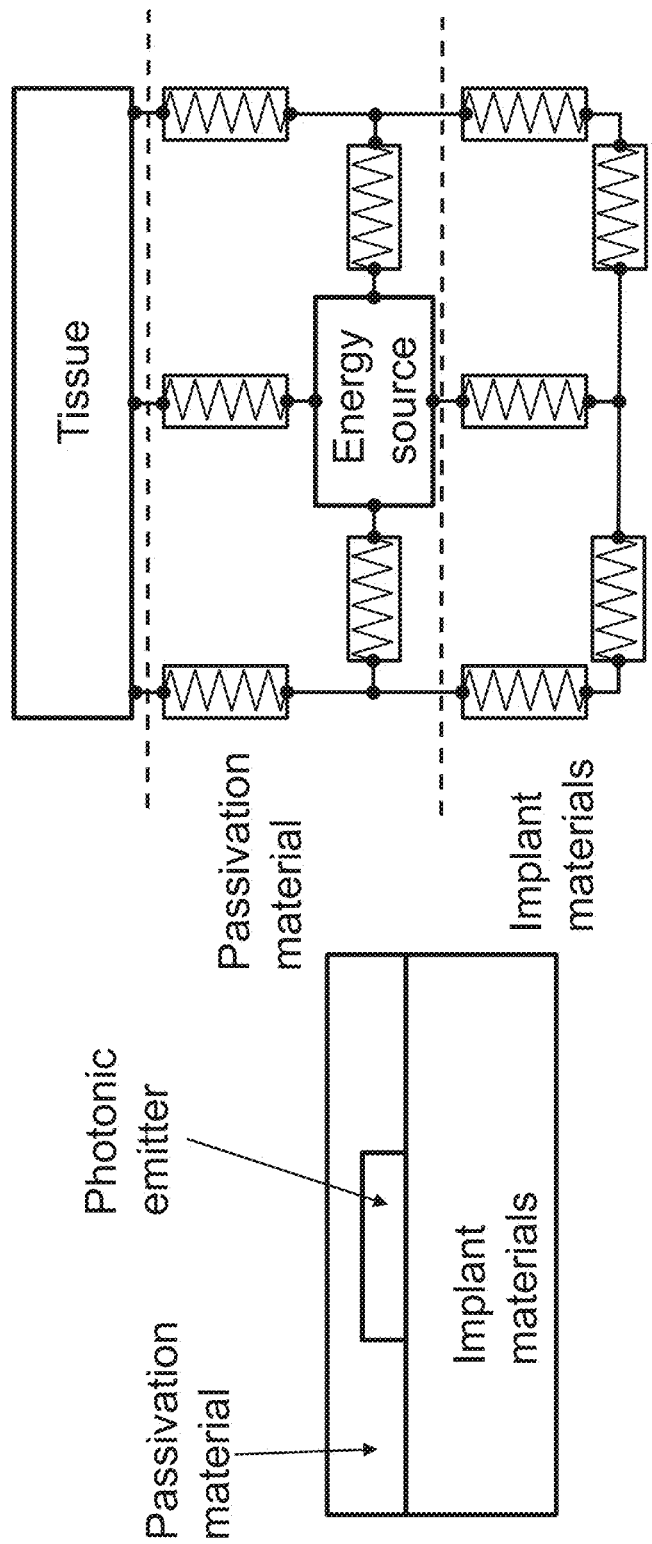
Figure 9c – thermal model

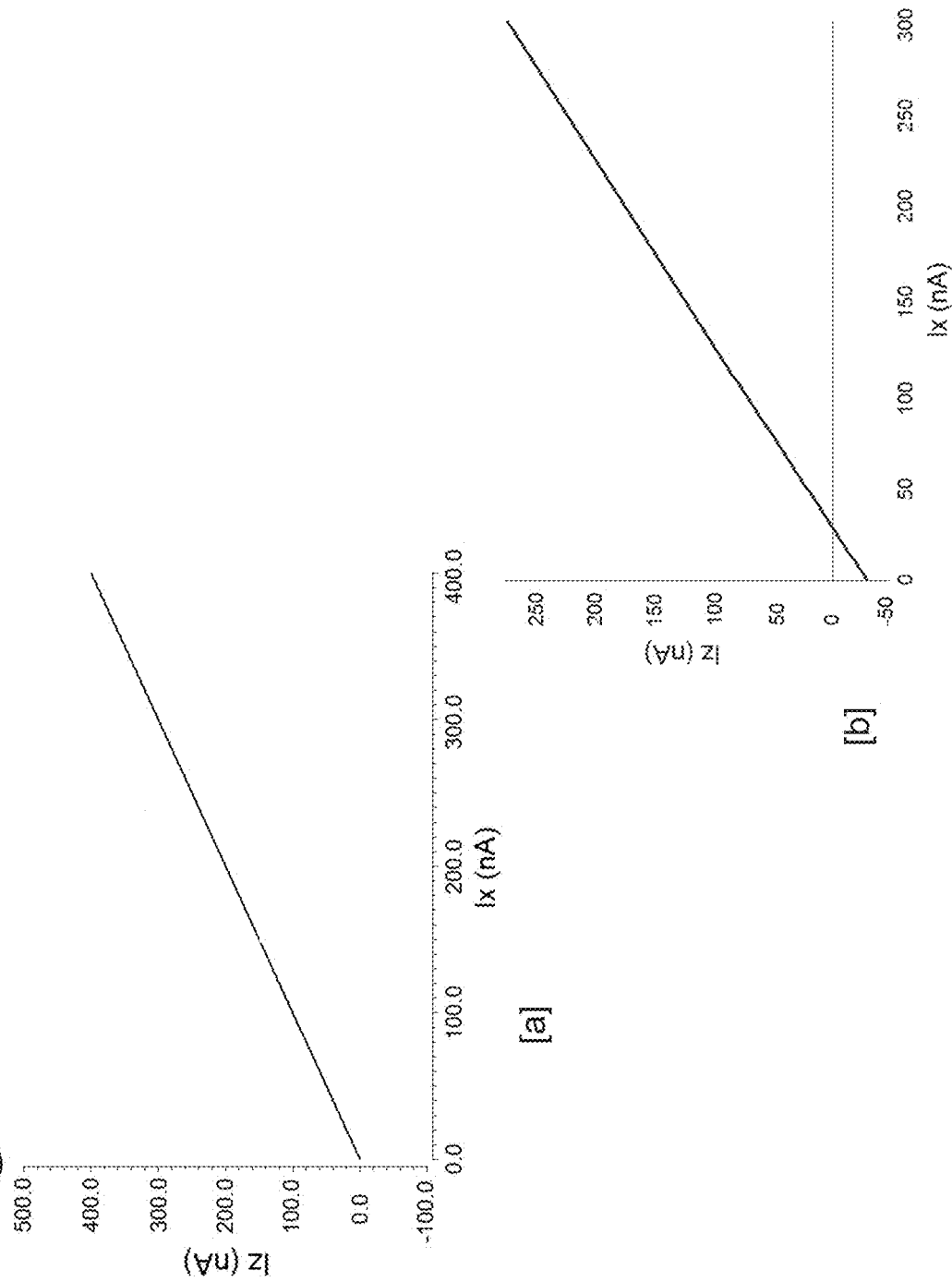

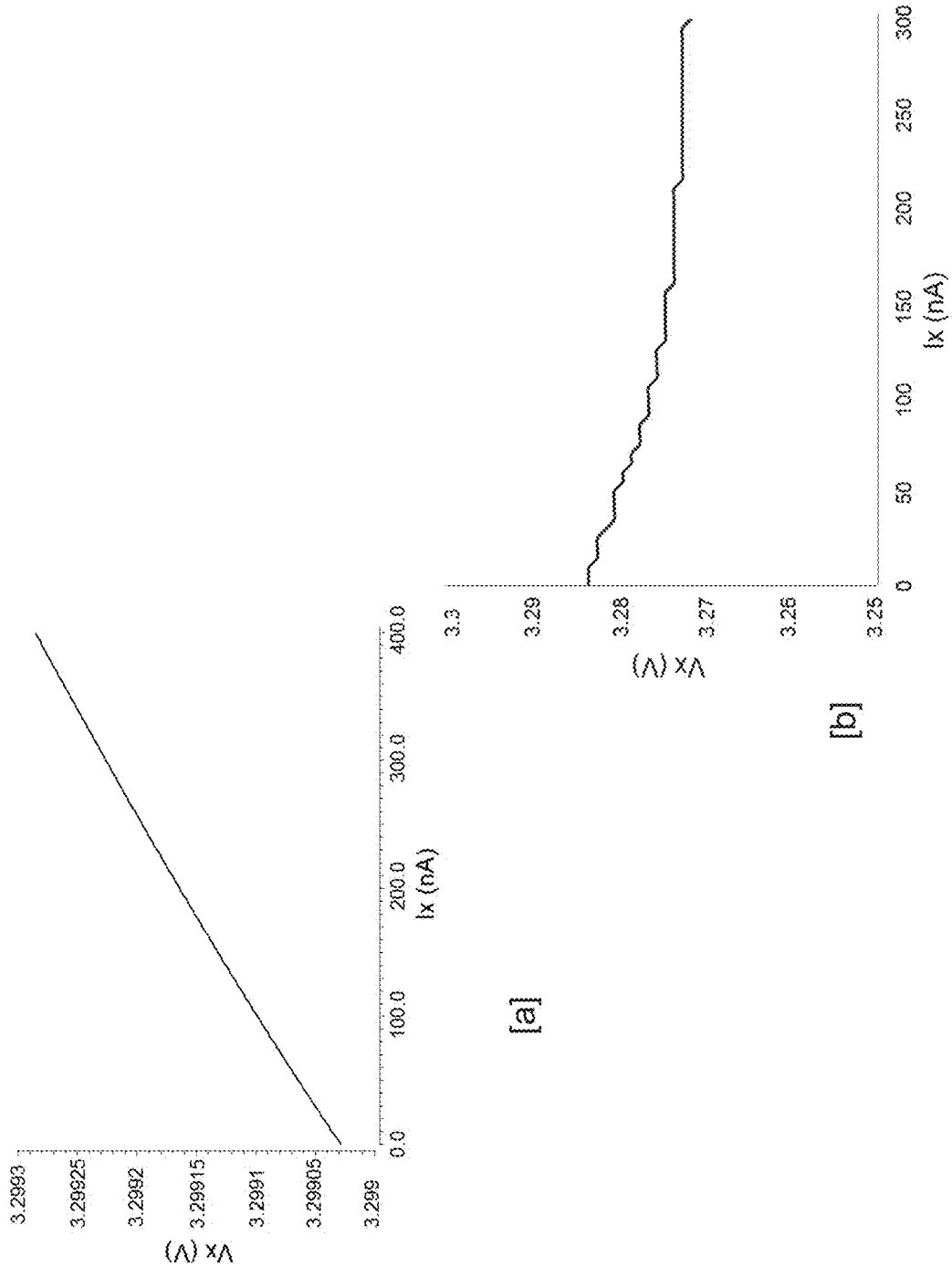

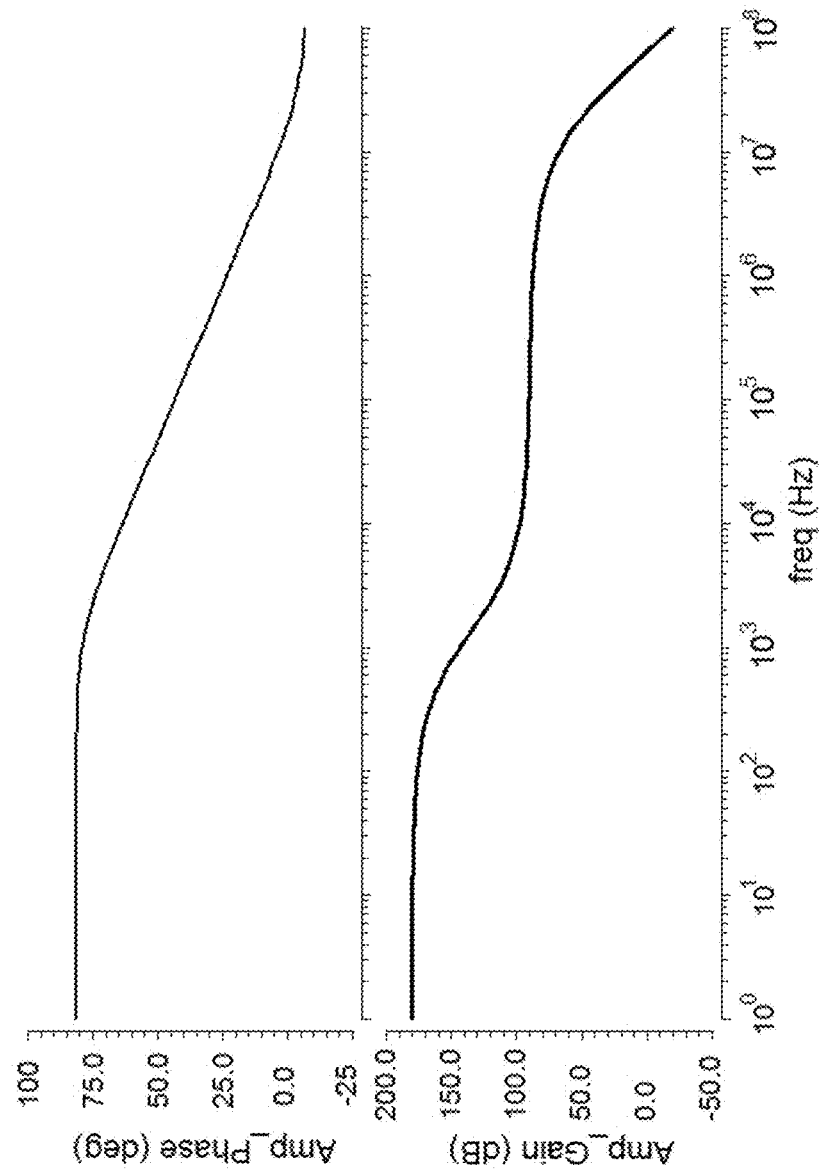

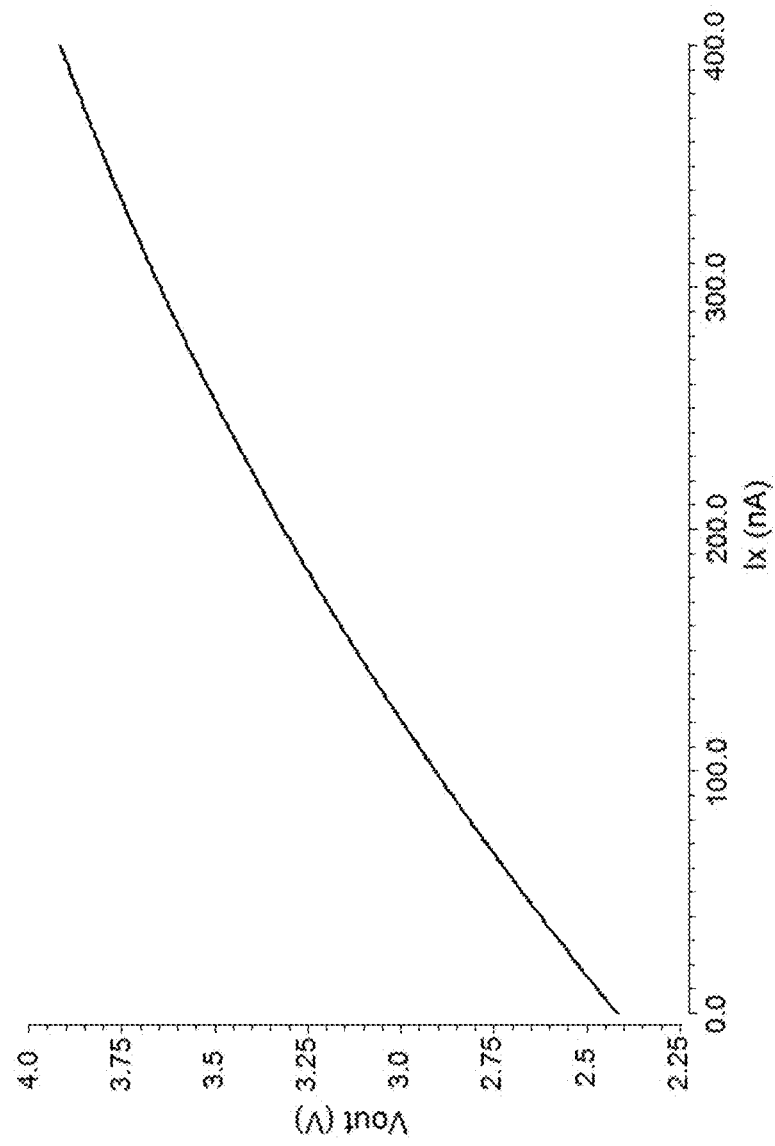
Figure 13 – Amplifier output

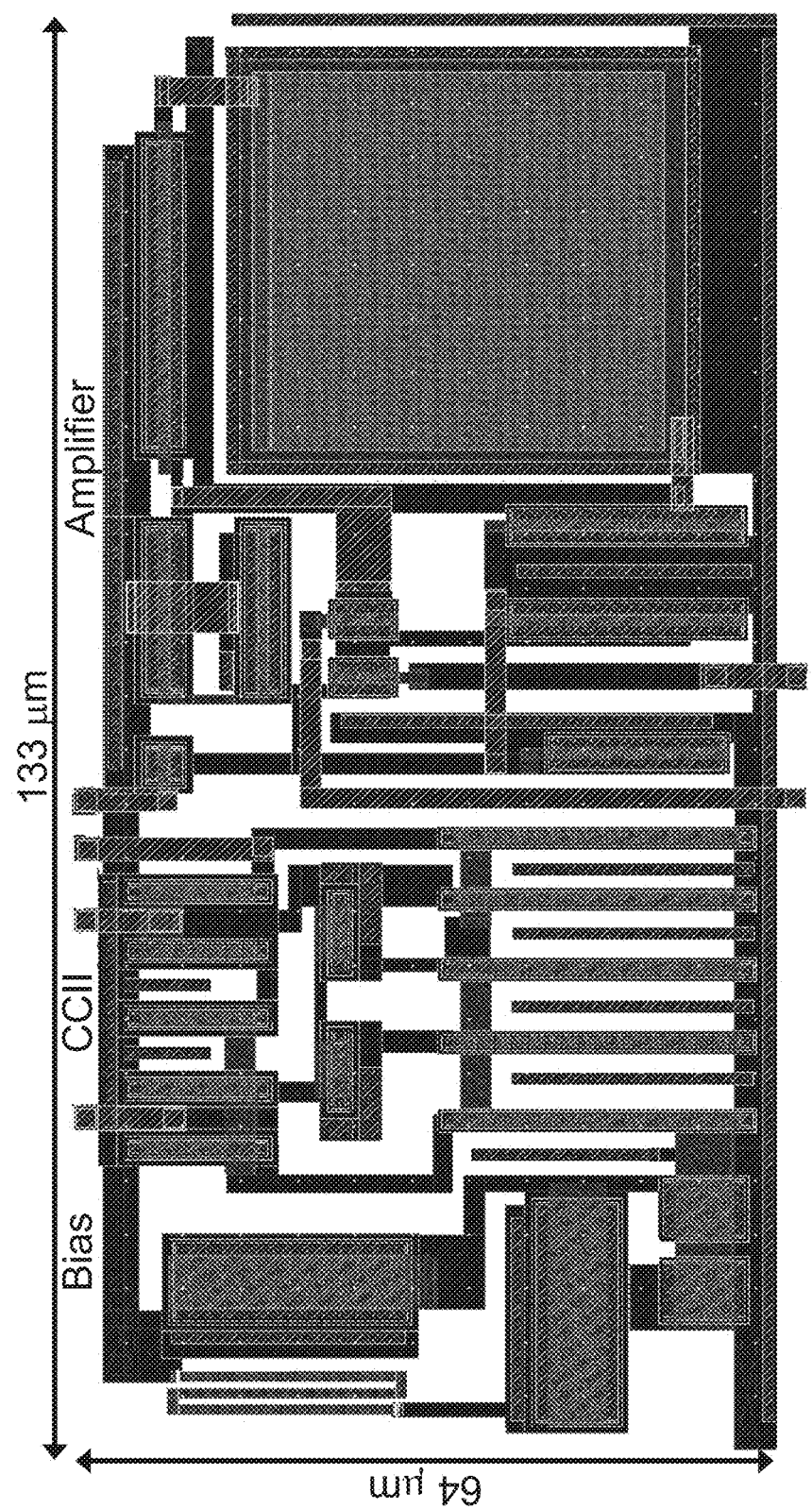
*Figure 14 – Layout*

TEMPERATURE SENSOR

CROSS-REFERENCE TO RELATED APPLICATIONS

The present application is a U.S. National Stage Application of PCT/EP2016/082433, filed Dec. 22, 2016; which claims priority to GB Application No. 1522790.3, filed Dec. 23, 2015.

FIELD OF INVENTION

The present invention relates to temperature sensors and methods of sensing temperature. The invention relates in particular, but not exclusively, to temperature sensors integrated with implantable devices.

BACKGROUND

Implantable devices are becoming increasingly important in clinical practice. A key target area is in treating neurological deficit. For example pacemakers have been utilized since the 1950's to support proper function of cardiac muscle and have more recently been applied to the brain to treat tremor in conditions such as Parkinson's disease. Beyond neuroprosthetics there is also a need to monitor and stimulate other organs such as the Pancreas in the case of diabetes.

Optical interrogation of cells and tissue has long been an important tool in ex-vivo studies. For example tissue staining methods have been around since the late 19th century. In the context of modern biomedical implantable devices, there are two key applications: opto-electrophysiology, and fluorescence sensing. The former allows control and recording of electrical activity in tissue. The latter can be used to explore chemical changes in cells or their environment.

The advent of opto-genetic reporters such as green fluorescent protein in the 1990's [1] have allowed imaging of the presence (or lack of) specific cell types. More recently functional derivatives allow for the opto-genetic imaging of cellular function and in particular, electrical function. For example, Ohiem et al. [2] have developed a red-fluorescent optogenetic calcium indicator which can be genetically inserted into cells to determine the level of calcium function. Calcium is an important chemical in many cellular processes and can be used to interrogate both the relative level of activity of neuron cells and more subtle biochemical changes in many cell types. Chemical reporters also exist, but these are less desirable as they would need to be continuously infused either because the optically active proteins bleach, or because ligand molecule which attaches them to the target cell breaks. In contrast genetically encoded reporters are continuously produced/recycled by their host cells.

In addition to optical recording, optical stimulus is possible through optogentic and optochemical methods. Traditional optochemical methods have utilized cage structures around a bio-active initiator molecules e.g. caged glutamate. In such structures, ltraviolet light is used to uncage the active part of the molecule and thus biomchemically activate the target cell (e.g. Shoham et al. [3]). This is problematic in-vivo so more recent methodologies have utilized lock and key approaches with photoconformable molecules. E.g. Broichhagen et al. utilize such approaches to insulin secretion [4]. However, perhaps the most useful method is optogenetics. In this case, cells are genetically modified to continuously produce optically sensitive proteins. Thus, there is no subsequent need to pump continuous biochemicals into the body. Such optogenetic stimulation can use either channelrhodospsins—light sensitive cation channels [5], halorodopsins—light sensitive ion pumps [6], or melanopsins—light sensitive G-protein coupled receptor systems [7]. Each has their own relative advantages and a good review of the field has be written by J. Barrett et al. [8]. What is common to all of these approaches is that they require high intensity irradiation of the optical targets. Furthermore the fundamental optically active cores in all of these proteins are derived from conjugated small molecules which are optically active in the ultraviolet (350 nm to orange/red 600 nm) region of the electromagnetic spectrum. In particular, blue wavelengths in this range are heavily scattered by neural tissue. This means there is a requirement for light delivery in close proximity to these targets. This can be achieved by one of two methods:

1. Light can be generated at some distance and then guided to the local position using optical confinement (e.g. optic fibre or waveguide) until the point of delivery.
2. Light can be produced locally by a penetrating or otherwise implantable device incorporating a microphotonic element close to the required target.

Each of these approaches has its relative advantages and disadvantages. In the case of optical delivery to the target, it can be challenging to multiplex large numbers of independent signals in a single system. Furthermore the light generator will still be implantable and will still generate heat, albeit perhaps from a domain than can better tolerate thermal load. In the case of microphotonic generation close to the target, the key issue is the formation of localized hot spots close to the biomedical device surface. A demonstration of such a hotspot can be seen in FIG. 1, which shows hot spot formation in implantable optrodes. On the left: an implantable optrode which is capable of delivering both optical emission and electrical recording. In the centre: a testing methodology in air utilising photodiode and infra-red camera. On the right: the temperature increase if two of the incorporated micro-LEDs are illuminated continuously.

Clearly, if implantable microphotonic components are illuminated at high radiance, there is the potential for significant heating at the device surface. However, for chronic implants, the raising of ambient temperature in surrounding tissue is undesirable. The current literature is not entirely clear on what long term effects could result from such temperature increase. What is known is that beyond 5° C. irreversible damage is done in acute experiments [9]. Additionally, as temperature raises beyond 1° C. signaling in the surrounding neural cells may be affected. The human body undergoes regular illness and recovery cycles within which fevers raise body temperatures by a few degrees with no long term ill-effect. However, even at the best of circumstances, there is typically some scar tissue formation around long term implants. This could be worsened by temperature increases. Furthermore raised surface temperatures on biomedical implants could engender inflammatory responses. In turn long term inflammatory responses have been linked to genetic mutations and tumor formations.

So clearly it would be desirable to monitor device temperatures and ensure they are maintained within desirable limits (e.g. T<39 C, dT<2 C above ambient).

There are a number of configurations for illuminating target tissue from photonic implants, as shown in FIG. 2. The use depends on the target application. For nerve bundles, cuff style optrodes which can wrap around the bundle are more appropriate (FIG. 2a). For direct stimulation of tissue from the surface, a planar structure is more appropriate (FIG. 2b). For deep penetration of tissue, penetrating optrodes either in single (FIG. 2c) or in array formation are most appropriate (FIG. 2d).

On-chip temperature sensors have been used to monitor human health for diseases diagnosis and treatment. For example, the adaptive multi-sensor CMOS system proposed by Huang et al. [10] comprises different on-chip sensors including temperature sensor. This device is capable of body temperature sensing from 32° C. to 42° C. and also environmental temperature sensing outside the body from −20° C. to 120° C. Lee et al. presented a low-cost CMOS thermal sensor chip for biomedical application to monitor temperature from 33° C. to 42° C. with less than 0.15° C. inaccuracy [11]. In their work, bipolar transistors are used to sense temperature and generate the needed reference voltage for sigma-delta analog to digital converter. Crepaldi et al proposed a low power CMOS based front-end thermal sensing element with 0.24° C. inaccuracy suitable for biomedical application [12].

The downside of using additional sensors is that they take additional surface space and need additional address architectures. This may thus present difficulties to integration. Furthermore, it increases the complexity and thus cost of fabrication. Perhaps most significantly by having separate sensors for temperature, there is always a danger that failure in the sensor may provide inaccurate readings; perhaps stating that the temperature rise is limited when the opposite is the case.

SUMMARY OF INVENTION

In general terms, the present invention proposes to use a light emitter (e.g. a microphotonic component such as a micro LED or laser diode) itself as its own thermal sensor. By utilizing the emitter as its own temperature sensor, the continued functionality of the device is intrinsically linked to its self-diagnosis.

In general terms we present a method to determine the temperature of microphotonic medical implants. The proposal is to use the photonic emitter as its own sensor and develop readout circuitry and models to accurately determine the surface temperature of the device. There are two primary classes of applications where microphotonics could be used in implantable devices; opto-electrophysiology, and fluorescence sensing. In opto-electrophysiology, optical methods such as optogenetics are used to provide optical stimulus and/or optical recording of cellular electrical activity. In Fluorescence sensing—the biochemical environment is optically probed with either fluorescence reporter proteins or via cellular autofluorescent signatures. In such scenarios light needs to be delivered to the nervous tissue. The optically sensitive proteins used in such applications typically tend to be sensitive in the photonic region of UV (350 mm) to red (600 nm). In this region scattering processes dominate optical traversal of tissue and thus light delivery systems need to be utilized. One key form of such a system is to generate light directly, but this can cause localized heating effects at the device surface which may need to be monitored. This invention allows such monitoring utilizing the heat producing device itself as a sensor, combined with specific electronic control and signal post-processing.

In a first aspect the invention provides a temperature sensor comprising:
 a light emitter;
 an electrical circuit for applying a reverse bias voltage across the light emitter and for measuring a reverse current; and
 means for calculating a temperature from the measured reverse current.

The means for calculating a temperature from the measured reverse current may include a predefined correlation of reverse current versus temperature for the light emitter.

The temperature that is calculated may a junction temperature of the light emitter or a surface temperature of the light emitter, for example. In the case where the temperature is surface temperature of the light emitter, it may be calculated, for example, using a model that relates surface temperature to the junction temperature of the light emitter (where that is calculated first) or directly to the measured reverse current. The model parameters will typically be determined by the implant mass and thermal properties relative to the passivation material. As an alternative example, the surface temperature may be calculated using a transfer function to determine the surface temperature based on a current/voltage measurement from the light emitter.

In some embodiments, the electrical circuit is configured to maintain the bias voltage at a constant value between 0 and 5V in reverse bias across the optical device.

In some embodiments, the light emitter is a microphotonic component, for example a light emitting diode or a stimulated emission device such as a semiconductor laser diode (e.g. in the form of a vertical cavity surface emitting laser). Where the light emitter is a microphotonic component it may be formed, for example in Gallium Nitride, Silicon Carbide, Aluminum Nitride, Indium Nitride, Gallium Phosphide, Aluminium Phosphide, Zinc Sulphide, Magnesium sulphide, Magnesium selenide, or Zn Selenide.

In some embodiments, the reverse bias voltage is maintained within +/−5% of a target bias voltage.

In some embodiments, the electrical circuit comprises one or more low pass filters to filter switching noise, whereby the photonic device temperature can be accurately determined despite variations in power supply noise.

In some embodiments, the light emitter has two modes of operation, a temperature sensing mode when a reverse bias voltage is applied across the light emitter and a light emission mode when a forward bias voltage is applied across the light emitter. The temperature sensor may be controlled to switch back and forth between the temperature sensing mode and the light emitting mode at a predefined frequency, for example from 1 GHz to 10 Hz. High frequencies (e.g. 1 MHz-1 GHz) typically encompass short pulses (e.g. 1 ns-1 μs), useful for instance for fluorescence lifetime sensing measurements of tissue. Low frequencies (e.g. 10 hz-1 MHz) typically encompass longer pulses (e.g. 100 ms-1 μs) useful for instance for optical (primarily neural) tissue stimulation.

In some embodiments, the temperature sensor can additionally be switched to an off mode in which no voltage is applied across the light emitter.

In some embodiments, the temperature sensor includes a controller for switching the temperature sensor between modes. The controller may, for example be configured (e.g. programmed) to switch the temperature sensor between modes at defined time points, pulse widths and/or repetition frequencies. The controller may additionally or alternatively be configured to stop subsequent operation in the light emission mode if the calculated temperature exceeds a predefined threshold. The predefined threshold may, for example, be in the range 0.1 to 3 C above the ambient temperature of the tissue.

In some embodiments, the forward bias voltage is in the range 1.5V-10V. Typically the selected forward bias will depend on the light requirement and optical wavelength. Shorter wavelengths generally need higher bias, as do higher intensities.

In some embodiments, the current in the forward bias is between 1 uA to 50 mA, dependent on the microphotonic size and required radiant density.

In a second aspect, the invention provides an implantable biomedical device incorporating a temperature sensor according to any one of the preceding claims.

The device may, for example, be for optogenetic stimulus of nervous function, wherein the light emitter of the temperature sensor performs optogenetic stimulus when the light emitter is in the light emission mode. In the light emission mode the light emitter of the temperature sensor may perform optogenetic stimulus of electrical activity or chemical activity indirectly via opto-electrical stimulus in non-nervous cells and/or tissue. The device may be operable to record cellular electrical or calcium potential in nervous and/or non-nervous tissue.

In a third aspect the invention proposes use of a microphotonic component to measure temperature, for example by applying a reverse bias across the microphotonic component, measuring a reverse current and calculating a temperature from the measured reverse current.

BRIEF DESCRIPTION OF FIGURES

An embodiment of the invention is described below with reference to the accompanying figures, in which:

FIG. 1 shows hot spot formation in implantable optrodes. Left an implantable optrode which is capable of delivering both optical emission and electrical recording. Centre a testing methodology in air utilising photodiode and infra-red camera. Right the temperature increase if two of the incorporated the micro-LEDs are illuminated continuously;

FIG. 2 shows Formats of optical interrogation of neural tissue (a) cuff optrode (b) planar surface emitting optrode array (c) penetrating singular optrode (d) penetrating optrode array;

FIG. 3 shows Measurement results achieved for GaN LED (a) absolute reverse current versus temperature in different bias voltages and (b) revers current versus voltage in different temperatures. Note how the reverse current increases much more significantly with reverse bias;

FIG. 4 shows Multiple quantum well architecture of LEDs and VCSEL lasers (a) band diagram without doping (b) band diagram with doping;

FIG. 5 shows (a) Active optrode including temperature sensor and (b) Exemplar penetrating biomedical device for applications in central nervous tissue;

FIG. 6 is a Block diagram of the proposed temperature sensor;

FIG. 7 is an Exemplar embodiment of the sensing architecture at a transistor level;

FIG. 8(*a*) is a block diagram of the LED employment for light emission and temperature sensing functions; and FIG. 8(*b*) is timing diagram of the applied signals to the LED for light emission and temperature sensing;

FIGS. 9(*a*) and 9(*b*) schematically show the approach to sensor control and FIG. 9*c* show a temperature model;

FIG. 10 shows Current gain of the designed CCII (Iz/Ix). The designed CCII should deliver the received current to its output with a linear gain in a wide range of input current (a) simulation results (b) experimental results FIG. 10 shows Current gain of the designed CCII (Iz/Ix). The designed CCII should deliver the received current to its output with a linear gain in a wide range of input current (a) simulation results (b) experimental results;

FIG. 11 shows Voltage of terminal X in CCII (Vx) which is used as reference voltage, 3.3V to bias the LED at its anode (a) simulation results (b) experimental results;

FIG. 12 shows Frequency analysis response for the amplifier in the last stage of the sensor with high gain;

FIG. 13 shows amplifier output for a specific CCII load versus input current of CCII; and FIG. 14 Layout of the designed temperature sensor including bias circuit, CCII and amplifier.

DETAILED DESCRIPTION

Utilising Microphotonics to Measure Own Junction Temperature

There are two primary forms of microphotonic emitters that could be used for useful optical interrogation of biological tissue:

1. Micro-sized light emitting diodes, primarily those utilising multi-quantum well (MQW) structures to ensure high efficiency optical emission.
2. Micro-sized stimulated emission devices i.e. lasers, with the most promising candidates being vertical cavity surface emitting lasers.

The optically active core material of these emitters could comprise of Gallium Nitride, Silicon Carbide, Aluminum Nitride, Indium Nitride, Gallium Phosphide, Aluminium Phosphide, Zinc Sulphide, Magnesium sulphide, Magnesium Selenide, or Zn Selenide depending on the desired optical properties. An example of the use of Gallium Nitride diodes for optical interrogation of astrocyte tissue can be seen in Berlinguer et al [13].

Vertical cavity surface emitting lasers are still in their infancy. Recent examples include a recent VCSEL developed by Wen-Jie Liu at Xiamen University [14]. Such devices are still in their infancy, but at their core is a fundamentally similar semiconductor structure to the light emitting diode. As the charge generation and current flow in all diodes is temperature dependent they may be used to detect the junction temperature, and from there infer the surface temperature of a given device.

In forward bias the LED current will exponentially increase with voltage. The current levels are thus high and will result in light emission (and thermal emission). Thus, from the perspective of diagnostics switching the diode into reverse bias allows interrogation of current level within a specific voltage domain. Currents in the reverse bias case are low and do not lead to perceptible light emission under normal voltages.

FIG. 3 shows the results achieved from a standard Gallium Nitride micro-LED incorporating a multiple quantum well architecture. The reverse current of such LEDs change linearly with temperature for a fixed bias voltage (FIG. 3*a*), but exponentially with reverse bias (FIG. 3*b*).

Theoretical Investigation

At a first approximation, an LED per definition is a light emitting diode. The diode structure consists of p and n doped layers which are combined in a p-n junction structure. The Shockley equation for a p-n junction given by (1) is used to derive the temperature dependency of the reverse current.

$$I = I_S\left[\exp\left(\frac{eV}{nkT}\right) - 1\right] \quad I = I_S\left[\exp\left(\frac{eV}{nkT}\right) - 1\right] \quad (1)$$

where I is the junction current, $I_S$ is the saturation current, e is the elementary charge, V is the junction voltage, n is the ideality factor which is about 1-2, k is the Boltzmann constant, and T is the absolute temperature in kelvins [10-12]. The LED saturation $I_S$ current can be expressed by $$I = eA\left[\sqrt{\frac{D_n}{\tau_n}}\frac{1}{N_D} + \sqrt{\frac{D_p}{\tau_p}}\frac{1}{N_A}\right]N_C N_V \exp\left(\frac{-E_g}{hT}\right)\left[\exp\left(\frac{eV}{nkT}\right) - 1\right] \quad (2)$$

Here, A is the cross-sectional area of the p-n junction; $D_n$ and $D_p$ are diffusion constants for electrons and holes exhibiting a $T^{-1/2}$ temperature dependency; $\tau_m$ and $\tau_p$ are the minority carrier lifetimes for electrons and holes supposed to be temperature independent; ND and NA are doping concentration of donors and acceptors which are independent of temperature; $N_C$ and $N_V$ are effective densities of states at the conduction-band and valence-band with temperature dependency of $T^{3/2}$. $E_g$ is the energy bandgap given by:

$$E_g(T) = E_g(0) - \frac{\alpha T^2}{T + \beta} \quad (3)$$

where $E_g(0)$ is the energy bandgap in T=0 K and α and β are the Varshni parameters [15, 16]. The modelling results based on Eq (3) shows a linear relation for $I_R$-T in pn junctions when a constant reverse voltage is applied.

Multiple Quantum Well Structures

In practice the theoretical framework of LEDs is more complex. Fundamentally, LEDs generate light by electron-hole recombination. Thus, the efficiency of light generation is a result of the percent of injected current (electrons and holes) which recombine to give our light compared to those that continue to the opposite terminal or recombine non-radiatevely. As a result, LED designers create a multiple quantum well structure with multiple layers of materials of different bandgaps to create trapping centres for recombination.

A quantum well is a heterostructure with one thin well layer surrounded by two barrier layers. Both electrons and holes are confined in the well layer which is so thin about 40 atomic layers. The quantum wells can be grown using molecular beam epitaxy (MBE) [17], and metal-organic chemical vapor deposition (MOCVD) [18]. The typical materials to be grown can be any sequence of GaAs, AlAs, and AlGaAs. The multiple quantum well layers act as trapping centres for charge mobility. Escape from such traps is therefore mediated primarily by thermionic emission and quantum tunneling (FIG. 4) over the traps. Both effects are temperature dependent [15, 19] resulting in a linear dependency within the temperature range interesting to this invention.

To summarize: Based on FIG. 3, it is very challenging to determine the junction temperature of an LED in reverse bias because the current rises considerably faster due to variations in bias than variations in temperature. Thus to achieve effective functionality, the LED must be interrogated at a fixed reverse bias which does not deviate in time or due to noise. Furthermore, although the light emitter will typically be close to the surface, what is being measured is the junction temperature rather than the surface temperature itself. A thermal model of how the LED sits in the host system must therefore be used to provide further accuracy in determining the surface temperature.

CMOS Temperature Sensor

FIG. 5 shows a single penetrating optrode with inbuilt stimulation and recording circuits along its shaft. The LED based temperature sensor circuitry is placed close to the μLEDs to be easily operating in antiphase with optical emission.

Experimental Verification

As the reverse current of LED is employed as temperature sensitive parameter to design the sensor we have experimentally explored GaN LEDs performance to investigate the linear relationship between junction temperature (Tj) and reverse current [15].

An LED test setup is implemented using GaN LED to extract the needed IR-T curve at different bias voltages. The LED under test is placed in an isolated dark box to guarantee that the measured current is only due to the temperature change. The box is also temperature isolated to ensure about the accuracy of the measured temperature. A hot plate is placed under the LED to increase the temperature which can be measured and recorded by the IR Optris PI camera and the camera interface software, respectively.

In a fixed reverse bias voltage across the LED, temperature is increased using the hot plat from 28° C. to 60° C. and the reverse current is measured. The measurement has been repeated for different bias voltages from −1.0V to −2.2V.

The results achieved from the LED testing experiment are shown in FIG. 3. The reverse current of LED is changing linearly with temperature for a fixed bias voltage. On the other hand, the reverse current changes with voltage in a fixed temperature. In other word, a variant or temperature dependent bias voltage can cause a large reverse current variation which is not purely related to temperature variation. As a result the designed temperature sensor should provide a fixed temperature independent bias voltage for the LED to avoid current variation because of bias voltage variation.

Sensor Structure

FIG. 6 depicts the block diagram of the proposed temperature sensing system based on LED. The designed sensing system measures the reverse current of the LED which is reversely biased using a bias voltage. Temperature variation linearly changes this reverse current if a fixed bias voltage is applied across the LED. The bias voltage must be precise and temperature independent not to contribute in reverse current changing because the reverse current can change with bias voltage significantly. Therefore, a circuit is needed to provide the bias voltage across the LED and receive its current in same time. For this purpose, a second generation current conveyor (CCII) is used at the first stage of the sensor which is capable of providing a precise bias voltage at the input (X) while receiving current using the same input terminal. In other word, CCII conveys the received current from LED to the output (Z). The CCII receives an external bias voltage in other input (Y) and copies this voltage on the input (X) which is supposed to be connected to LED and receive the reverse current. In this design VX is match to VY and the output current should follow the current at the input (X).

A unity current gain for a range of frequencies is needed for the CCII to accurately translate the current changes to temperature variation in the next stages. Also, linearity is important for a specific input range of reverse current.

Therefore, a robust bias voltage, unity current gain, linearity and low power are the most important specifications in designing the CCII.

A resistor is used to convert the CCII out current to voltage to be amplified using the amplifier in the last stage. The designed amplifier is a single input single output high gain amplifier. This amplifier receives the current variation as voltage in the input and amplifies that to a large signal suitable to digitize using ADC.

The most important parameters in the design of this amplifier are high gain, low power, high dynamic range, high CMRR and PSRR. The common mode rejection properties are determined by matching of transistors and in particular, matching at the input differential stage. This is achieved through enlarging transistors and performing Monte Carlo modelling at the design stage to ensure a probabilistic match. Similarly, the use of larger transistors supports the low pass filtering to reject high frequency power supply noise. A negative feedback loop is utilised to support high gain and thermal noise rejection.

An exemplar of our designed sensor was created using a standard CMOS (Complementary Metal Oxide Semiconductor) process from Austra Microsystems. The technology node was 0.35 μm and standard CAD/EDA tools were utilised for its design. The schematic of the design is shown in FIG. 7. The CCII at first stage receives the LED current in terminal X which has the same vdd voltage as input Y. The received current is copied to the output Z connected to a resistive load [20]. The second stage includes a two-stage high gain amplifier.

Operation

The sensor circuitry is placed close to the LED which is easily operating in antiphase with optical emission done using stimulation circuits. Temperature sensing is supposed to be performed after LED light emission. In other word, forward biased LED emits light where its intensity can be controlled using pulse width modulation. Then, switching the LED in to the sensor path provides reverse bias for the LED using a specific voltage reference (FIG. 8).

Table 1 lists different examples for LED timing operation. PW1 is used to stimulate the LED by providing the forward bias. After this operation, temperature sensing will be performed to sense the temperature around the LED and its variation by operating in different time slots after LED stimulation.

Stimulation duration (PW1) should be enough to do the LED stimulation and provide the required light intensity. Therefore, PW1 is chosen based on the applied signal as bias to the LED, its specification and the required light intensity. Sensor operation time (PW2) should be enough to do temperature sensing operation and in same time small enough to decrease the overall power consumption in the system as the amplifier of the sensor is the most power consuming part of the design.

TABLE 1 exemplar timing operation for stimulating the LED with PW1 and then sensing the temperature with PW2

| Frequency (Hz) | T (msec) | PW1 (msec) | Duty cycle1 | PW2 (msec) | Duty cycle2 |
|---|---|---|---|---|---|
| 5 | 200 | 10 | 5% | 2 | 1% |
| 10 | 100 | 10 | 10% | 2 | 2% |

Creating a Transfer Function for the Control Unit

The proposed sensor measures the LED junction temperature. A thermal model is needed to be developed to perform final optimisation of the results to accurately determine the surface temperature of the device as opposed to the junction temperature of the light emitter. This modelling can be performed using finite element tools such as COMSOL Multiphysics. A model can be built up using the LED layer materials, implant host materials and passivation cladding materials. Provided the layers are appropriately determined, the host implant should act as a heat sink to distribute heat along its bulk and then surface to prevent hot-spot development. Nevertheless this will still occur at sufficient intensities and pulse durations, necessitating this invention. The model itself can be built up of thermal resistive elements for the materials and their dimensions. Once created a transfer function can be developed to determine what a specific junction temperature means in terms of surface temperature.

Once implemented on the control unit. The controller will define pulse periods for stimulus and tissue sensing. During these periods, there will be intermittent forward and reverse voltage polarities to determine the temperature during optical stimulus. Should the temperature not exceed a threshold, this will continue until the end of the tissue stimulus or sensing period. Alternatively, should the temperature exceed a defined threshold, then the control unit will stop the stimulus and a negative event logged for long term monitoring of the implant operation.

The value of the thermal resistance for the device can be used to calculate the device surface temperature based on the measured junction temperature. FIG. 9 shows the all steps needed to measure the junction temperature and surface temperatures and their variation.

Results

FIG. 10 shows the simulation and experimental results for the output current of the designed CCII versus input current. FIG. 11 shows the results for the voltage at terminal X of CCII which is expected to be 3.3V and act as reference voltage for the LED. The specifications achieved for CCII from simulation and experiments are almost matched and listed in Table 2.

TABLE 2

Design specifications for CCII

| Specifications @ Ix = 0~200 nA | Simulation results | Experimental results |
|---|---|---|
| Current gain | 1 | 1 |
| Vx/Vy | 3.299/3.3 | 3.275/3.3 |

FIG. 12 shows the frequency analysis response for the designed high gain amplifier. FIG. 13 shows the output voltage of the amplifier versus input current of CCII where a specific load resistor is placed at the output of CCII. This voltage is linear up to 200 nA for the LED reverse current.

The specifications of the designed amplifier and overall system are listed in Table 3 and Table 4, respectively. The overall gain of the sensing system is about 107V/A without taking amplifier in to saturation region. For small range of temperature variations and consequently small reverse current variations a higher gain can be chosen. The layout of the design is depicted in FIG. 14.

TABLE 3

Amplifier specifications

| Specifications | Simulation results |
|---|---|
| Gain | 86 dB |
| PM | 52° |
| BW | 1.5 kHz |

TABLE 4

Design specifications

| Specifications | Simulation Results |
|---|---|
| Supply voltage | 5 V |
| Power dissipation | 52 µA × 5 V |
| Overall gain | $10^7$ (V/A) |
| Size | 133 µm × 64 µm |

CONCLUSION

An LED-based temperature sensor in AMS 0.35 µm CMOS technology has been designed to detect temperature variations around the implanted micro-LEDs in biomedical applications like optogenetics. The modeling and measurements results for GaN LEDs show that the reverse current of the LED can be considered as a reliable temperature sensitive parameter to sense thermal variations-around the LED. The designed CMOS temperature sensor consisting of a second generation current conveyor and a high gain amplifier is capable to receive and amplify the small current variations up to 200 nA. These current variations will then be translated into temperature variations based on the applied reverse voltage. This proposed method of temperature sensing is area efficient by eliminating area consuming sensing blocks which are usually used for temperature sensing in implantable systems. Also, the danger of failure because of the other devices can be decreased.

Embodiments of the invention are described above by way of example only. The skilled person will appreciate that various modification can be made without departing from the invention.

REFERENCES

[1] R. Heim, A. B. Cubitt and R. Y. Tsien, "Improved green fluorescence," Nature, vol. 373, no. 6516, pp. 663-4, 1995.

[2] m. Oheim M, M. van't Hoff, A. Feltz and A. Zamaleeva, "New red-fluorescent calcium indicators for optogenetics, photoactivation and multi-color imaging," vol. 1843, no. 10, pp. 284-306, 2014.

[3] S. Shoham, D. H. O'Connor, D. V. Sarkisov D V and S. S. Wang, "Rapid neurotransmitter uncaging in spatially defined patterns," Nature methods, vol. 2, pp. 837-843, 2005.

[4] J. Broichhagen, T. Podewin, H. Meyer-Berg, Y. von Ohlen, N. R. Johnston, B. J. Jones, S. R. Baloom, G. A. Rutter, A. Hoffmann-Roder and D. Hodson, "Optical Control of Insulin Secretion Using an Incretin Switch," Angewandte Chemie International Edition, vol. 54, 2015.

[5] G. Nagel, T. Szellas, W. Huhn, N. Kateriya, N. Adeishvili and P. Berthold, "Channelrhodopsin-2, a directly light-gated cation-selective membrane channel," National Academy of Science, vol. 100, pp. 13940-13945, 2003.

[6] F. Zhang, L. Wang, M. Brauner, J. Liewald J, K. Kay, N. Watzke, P. Wood, E. Bamberg, G. Nagel, A. Gottschalk and K. Deisseroth, "Multimodal fast optical interrogation of neural circuitry," Nature, vol. 446, no. 7136, p. 633-639, 2007.

[7] A. Koizumi, K. Tanaka K F and A. Yamanaka, "The manipulation of neural and cellular activities by ectopic expression of melanopsin," Neuroscience Research, vol. 75, no. 1, pp. 3-5, 2013.

[8] J. Barrett, R. Berlinguer-Palmini and P. Degenaar, "Optogenetic approaches to retinal prosthesis," Visual Neuroscience, vol. 31, no. 4-5, pp. 345-354, 2014.

[9] T. Fujii and Y. Ibata, "Effects of heating on electrical activities of guinea pig olfactory cortical slices," European Journal of Physiology, vol. 392, no. 3, p. 257-260, 1982.

[10] Y. J. Huang, T. H. Tzeng, T. W. Lin and C. W. Huang, "A Self-Powered CMOS Reconfigurable Multi-Sensor," IEEE Journal of Solid-State Circuits, vol. 49, no. 4, pp. 851-866, 2014.

[11] H. Y. Lee, C. M. Hsu and C. H. Luo, "CMOS thermal sensing system with simplified circuits and high accuracy for biomedical application Circuits and Systems," in Proceedings of IEEE International Symposium on Circuits and Systems, ISCAS, 2006.

[12] P. C. Crepaldi, R. L. Moreno and T. C. Pimenta, "Low-voltage, low-power, high linearity front-end thermal sensing element," Electronics Letters, vol. 46, no. 18, pp. 1271-1272, 2010.

[13] R. Berlinguer-Palmini, R. Narducci, K. Merhan, A. Dilaghi, F. Moroni, A. Masi, T. Scartabelli, E. Landucci, M. Sili, A. Schettini, B. McGovern B and G. Mannaioni, "Arrays of MicroLEDs and Astrocytes: Biological Amplifiers to Optogenetically Modulate Neuronal Networks Reducing Light Requirement," PLoS One, vol. 9, no. 9, 2014.

[14] e. a. Liu, Applied Physics Letters, vol. 104, no. 251116, 2014.

[15] B. Wu, S. Lin, T. M. Shih, Y. Gao, Y. Lu, L. Zhu, G. Chen and Z. Chen, "Junction-Temperature Determination in InGaN Light-Emitting Diodes Using Reverse Current Method," IEEE Transaction on Electronc Devices, vol. 60, no. 1, 2013.

[16] Y. Xi and E. F. Schubert, "Junction-temperature measurement in GaN ultraviolet light-emitting diodes using diode forward voltage method," APPLIED PHYSICS LETTERS, vol. 85, no. 12, pp. 2163-2165, 2004.

[17] A. Y. Cao, "Advances in molecular beam epitaxy (MBE)," Journal of Crystal Growth, vol. 111, no. 1, pp. 1-13, 1991.

[18] K. Furuya and Y. Miyamoto, "GaInAsP/InP organometallic vapor phase epitaxy for research and fabrication of devices," International Journal of High Speed Electronics, vol. 1, no. 347, 1990.

[19] X. A. Cao, E. B. Stokes and P. M. Sandvik, "Diffusion and Tunneling Currents in GaN/InGaN Multiple Quantum Well Light-Emitting Diodes," IEEE ELECTRON DEVICE LETTERS, vol. 23, no. 9, 2002.

[20] S. B. Salem, M. Fakhfakh, D. S. Masmoudi, M. Loulou, P. Loumeau and N. Masmoudi, "A High Performances CMOS CCII and High Frequency Application," Analog Integrated Circuits and Signal Processing, vol. 49, pp. 71-78, 2006.

The invention claimed is:

1. An implantable biomedical device for optogenetic stimulus of nervous function, the implantable biomedical device incorporating a temperature sensor, the temperature sensor comprising:
a microphotonic light emitter comprising a junction between two materials and having a light emission mode for optogenetic stimulation;
an electrical circuit for applying a reverse bias voltage across the light emitter and for measuring a reverse current; and
means for calculating a temperature from the measured reverse current;
wherein the electrical circuit comprises a second generation current conveyer configured for maintaining the reverse bias voltage within +/−5% of a target bias.

2. An implantable biomedical device according to claim 1, wherein the means for calculating a temperature from the measured reverse current includes a predefined correlation of reverse current versus temperature for the light emitter.

3. An implantable biomedical device according to claim 1, wherein the temperature that is calculated is a junction temperature of the light emitter.

4. An implantable biomedical device according to claim 1, wherein the temperature that is calculated is a surface temperature of the light emitter.

5. An implantable biomedical device according to claim 4, wherein the surface temperature is calculated using a model that relates surface temperature to a junction temperature of the light emitter and/or to the measured reverse current.

6. An implantable biomedical device according to claim 4, wherein the surface temperature is calculated using a transfer function to determine the surface temperature based on a current/voltage measurement from the light emitter.

7. An implantable biomedical device according to claim 1, wherein said electrical circuit is configured to maintain the bias voltage at a constant value between 0 and 5V in reverse bias across the optical device.

8. An implantable biomedical device according to claim 1, wherein the light emitter is a microphotonic component.

9. An implantable biomedical device according to claim 8, wherein the microphotonic component is a light emitting diode.

10. An implantable biomedical device according to claim 8, wherein the microphotonic component is a stimulated emission device.

11. An implantable biomedical device according to claim 10, wherein the stimulated emission device is a semiconductor laser diode.

12. An implantable biomedical device according to claim 8, wherein the microphotonic component is formed in Gallium Nitride, Silicon Carbide, Aluminum Nitride, Indium Nitride, Gallium Phosphide, Aluminium Phosphide, Zinc Sulphide, Magnesium sulphide, Magnesium selenide, or Zn Selenide.

13. An implantable biomedical device according to claim 1, wherein the electrical circuit comprises one or more low pass filters to filter switching noise, whereby a photonic device temperature can be accurately determined despite variations in power supply noise.

14. An implantable biomedical device according to claim 1, wherein the light emitter has two modes of operation, a temperature sensing mode when the reverse bias voltage is applied across the light emitter and a light emission mode when a forward bias voltage is applied across the light emitter.

15. An implantable biomedical device according to claim 14, wherein the temperature sensor is controlled to switch back and forth between the temperature sensing mode and the light emitting mode at a predefined frequency.

16. An implantable biomedical device according to claim 15, wherein said predefined frequency is from 10 Hz to 1 GHz.

17. An implantable biomedical device according to claim 14, wherein the temperature sensor can additionally be switched to an off mode in which no voltage is applied across the light emitter.

18. An implantable biomedical device according to claim 14, further comprising a controller for switching the temperature sensor between modes.

19. An implantable biomedical device according to claim 18, wherein the controller is configured to switch the temperature sensor between modes at defined time points, pulse widths and/or repetition frequencies.

20. An implantable biomedical device according to claim 18, wherein the controller is configured to stop subsequent operation in the light emission mode if the calculated temperature exceeds a predefined threshold.

21. An implantable biomedical device according to claim 20, wherein the predefined threshold is in the range of 0.1 to 3 C above an ambient temperature of the tissue.

22. An implantable biomedical device according to claim 14, wherein the forward bias voltage is in the range of 1.5V 10V.

23. An implantable biomedical device according to claim 14, wherein a current in the forward bias is between 1 uA to 50 mA.

24. An implantable biomedical device according to claim 1, wherein in the light emission mode the light emitter of the temperature sensor performs optogenetic stimulus of electrical activity or chemical activity indirectly via opto-electrical stimulus in non-nervous cells and/or tissue.

25. An implantable biomedical device according to claim 24, further comprising means operable to record cellular electrical or calcium potential in nervous and/or non-nervous tissue.

26. An implantable biomedical device for optogenetic stimulus of nervous function, the implantable biomedical device incorporating a temperature sensor, the temperature sensor comprising:
a microphotonic light emitter comprising a junction between two materials and having a light emission mode for optogenetic stimulation;
an electrical circuit for applying a reverse bias voltage across the light emitter and for measuring a reverse current; and
a model or transfer function for calculating a temperature from the measured reverse current;
wherein the electrical circuit comprises a second generation current conveyer configured for maintaining the reverse bias voltage within +/−5% of a target bias.

* * * * *